United States Patent [19]

Vogl et al.

[11] 4,126,789
[45] Nov. 21, 1978

[54] X-RAY PHANTOM

[76] Inventors: Thomas M. Vogl, 225 McClure Cir., Morehead, Ky. 40351; Evelyn L. Roberts, 492 S. Clarkson, Denver, Colo. 80209

[21] Appl. No.: 803,474

[22] Filed: Jun. 6, 1977

[51] Int. Cl.² ............................................. G02B 5/00
[52] U.S. Cl. .................................. 250/505; 250/252; 250/510
[58] Field of Search ............... 250/252, 312, 320, 321, 250/476, 510, 505

[56] References Cited

U.S. PATENT DOCUMENTS

| 3,348,319 | 10/1967 | Harrison | 250/320 X |
| 3,715,587 | 2/1973 | Burkhalter et al. | 250/510 X |

Primary Examiner—Davis L. Willis
Attorney, Agent, or Firm—Kyle W. Rost

[57] ABSTRACT

An X-ray phantom having a radiolucent sealed case contains sea water, a floatation chamber sealed against the sea water and having an exterior opening, and various X-ray calibration targets for illustration of a variety of densities and shapes for radiographic study.

10 Claims, 5 Drawing Figures

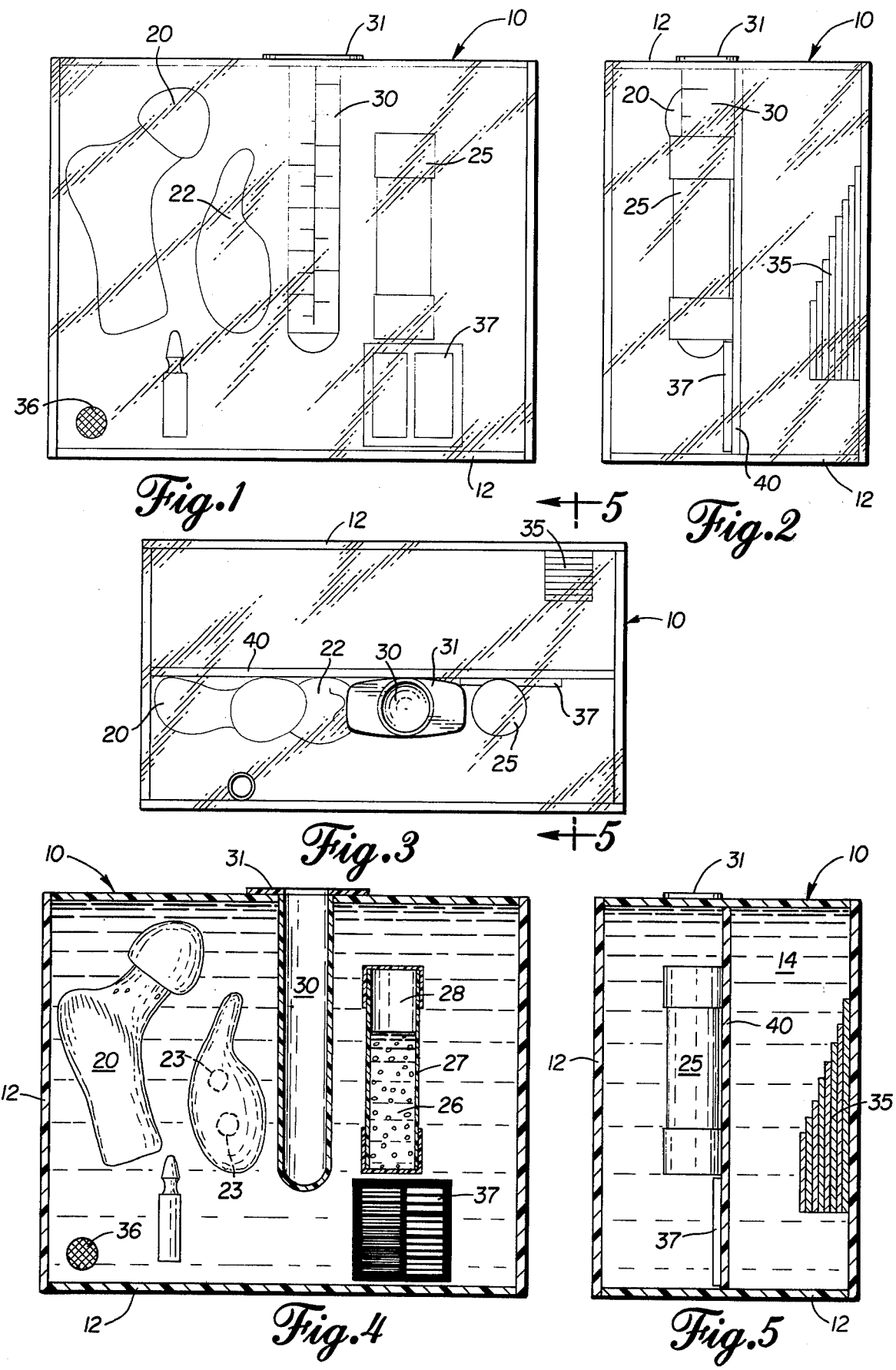

X-RAY PHANTOM

BACKGROUND OF THE INVENTION

1. Field of the Invention

The invention relates to X-ray machine calibration devices, and specifically in an improved X-ray phantom.

2. Description of the Prior Art

X-ray phantoms are known calibration devices and teaching aids for conventional X-ray machines. The prior art phantoms are available in a number of variations, some being plastic replicas of the human body or specific portions thereof, while others consist of actual human bones cast in plastic. These phantoms are used to train X-ray technicians in the proper positioning of the human body for the various X-ray pictures that are taken for diagnosis, and the resulting films may be studied to aid in calibrating the X-ray machine and identifying the radiographic image of known structures.

The structure of prior art phantoms has uniformly been solid, as taught in U.S. Pat. No. 3,348,319 to Harrison, A problem with any solid phantom is that the user is limited by those objects that the manufacturer has placed within it. In addition, the solid phantom is unlike the human body, which is mostly liquid and contains air spaces. In an effort to simulate the radioequivalent of the human body, manufacturers have tried many plastic materials and often have molded air spaces into a human replica.

One of the primary problems in the use of an X-ray machine is proper calibration. The radiation does must be adjusted for both proper penetrating power and intensity for each different application. The established setting for a given job may very with a different film, different film holder, or other equipment change. At times, a machine must be adjusted to locate a special object in a patient's body, such as broken needle or catheter. Traditional phantoms lack versatility for critical adjustment in these special situations.

Some of the other difficulties encountered with full-body phantoms include extremely difficult handling because of the weight of the synthetic construction materials; positioning of examinations of joints is limited because of metallic parts needed to hold the joints together, and these metallic parts interfere with the accuracy of the finished radiograph; the mock body organs placed is a solid phantom are not realistic and it is difficult to remove contrast media placed in these organs; the skeletons used in full body phantoms are osteoporotic and finished radiographs of the extremities lack proper radiographic contrast and density; and chest and abdomen also lack accuracy in radiographic contrast and density.

Some of the difficulties encountered with disarticulated phantoms such as bones cast in plastic include unrealistic radiographic density and contrast because of a lack of fatty tissue and gas patterns as are seen in human radiographs of the pelvis. There are generally only two densities in the radiographs of such phantoms: one for bone and one for overall soft tissue, the latter of which may be absent entirely. Skull phantoms lack significant air in the sinuses and mastoid cells to provide additional densities.

Many of the noted problems are directly related to the lack of a superior means of accurately simulating various densities found in the human body, while other problems relate to the difficulty in locating and removing contrast media and other desired subject matter in an environment simulating the human body. These problems and others are solved with the present x-ray phantom.

SUMMARY OF THE INVENTION

A radiolucent case contains a liquid scattering medium for x-radiation and has a plurality of solid objects mechanically suspended within the case. The liquid solution is roughly equivalent to human body fluids and the preferred liquid is sea water. The solid objects suspended in the case simulate a variety of subjects for x-ray investigation and also include useful x-ray machine adjustment and calibration aids to be studied as in the environment of a human body. Included in the solid objects may be a floatation chamber with exterior entry for allowing evaluation of an object of choice in the human body environment.

An object of the invention is to create an improved x-ray phantom that closely simulates the environment of the human body through use of a liquid that scatters x-radiation much as do the fluids of the body. Sea water has been found to be an exceptionally accurate substitute of the fluids of the body for purposes of simulating the interaction of x-radiation with the body.

Another object is to allow x-ray machine calibration by evaluating various calibration instruments within the simulated environment of the human body. X-ray machines are often calibrated by directly exposing a calibration device such as a step-wedge penetrometer to x-radiation and evaluating the machine adjustment by study of the resulting films. The present invention may include such a step-wedge penetrometer as a suspended object in the radiolucent, fluid filled case. When the machine is calibrated, the resulting film more accurately reflects how the actual x-ray of a human subject will appear with a given machine setting.

A further object is to allow x-ray machine adjustment for locating almost any object of special interest. Machine adjustment is critical when careful x-ray exploration is being conducted, and it is obviously in the best interests of the patient for the absolute minimum number of x-ray exposures to be taken in order to obtain needed information about the patient's internal conditions. For this reason, it is vital that a phantom approximate the x-ray response of the human body as closely as possible and that the targets within the phantom approximate the target of the actual x-ray investigation as closely as possible. When the object being sought within a human is, for example, a broken needle or piece of catheter, it is extremely difficult with presently available phantoms to accurately adjust the x-ray machine to locate the sought object. With the present invention, the sought object may be placed in a chamber within the phantom and the machine adjusted to find the object within the human body environment.

BRIEF DESCRIPTION OF THE DRAWINGS

FIG. 1 is a front elevational view of the phantom showing representative target objects contained therein.

FIG. 2 is a side elevational view of the phantom.

FIG. 3 is a top plan view of the phantom.

FIG. 4 is a front cross-sectional view showing the interior of several target objects.

FIG. 5 is a side cross-sectional view taken along the plane of line 5—5 in FIG. 3.

DESCRIPTION OF THE PREFERRED EMBODIMENT

The x-ray phantom 10 illustrated in the drawings includes a radiolucent case 12 containing a number of suspended objects useful in the adjustment of an x-ray machine. In addition, the case 12 is substantially filled with scattering medium 14 for x-radiation, preferably sea water or its equivalent. The entire phantom 10 may be used for x-ray photographs from any side or angle, depending on the particular requirements of a job.

Case 12 may be constructed of any radiolucent material, either visually transparent or opaque. A preferred material is a high impact plastic such as polycarbonate, but fiber glass is also suitable. The size of the case 12 is preferably close to the dimensions of portions of the human body so that the phantom will closely simulate the effect of the body on x-radiation. One set of preferred dimensions is eight inch width, ten inch length, and six inch depth. An optional compartment of similar width and length to case 12 but of reduced depth, containing the same scattering medium, may be used with the phantom 10 to illustrate the changes in film qualities due to increased thickness of a body part and the corresponding increase in scattered radiation.

The objects suspended in the case 12 are variable, but all benefit from the x-ray environment similar to that of a human body, and therefore, produce a far more useful image on film than would any of objects outside the phantom. The preferred contents include a sample of human bone tissue, for example the proximal end of the femur 20 or a lumbar vertebra (not shown). The utility of a bone sample is in adjusting the x-ray machine for common exposure of skeletal parts. Such exposure represents one of the basic uses of x-ray equipment.

A container of aqueous solution of iodine contrast agent 22 as is commonly used in the x-ray art is included as an aid in identifying human organs. Within container 22 illustrated as approximating the shape of a gallbladder, may be placed several small stones 23 of composition similar to gallstones. These stones 23 are best shown in FIG. 4, and represent a subject requiring careful machine adjustment for good x-ray pictures. Because phantom 10 may be x-rayed from any side or angle, the stones may be viewed in a variety of positions as they shift within container 22 according to its orientation with respect to the ground.

Another difficult x-ray job is locating polypoids, and container 25 is included to simplify the task. This container holds a contrast agent 26, such as barium sulfate, $BaSO_4$, suspended in a heavy medium such as heavy oil or molasses. The interior sides of container 25 support several modules 27 of dense material such as silicone rubber, which radiographically simulate occupying lesions, otherwise known as polypoids. Barium sulfate is a commonly used contrast agent in x-ray investigation of the digestive tract and it is used in container 25 to simulate the x-ray identification of polypoids in the intestines. Preferably, container 25 also contains air 28, allowing study of air/liquid interface in the various positions in which the phantom can be placed and from the various angles from which the x-ray photo can be made.

One of the important features of the present invention is flotation chamber 30 that extends into the phantom but has an exterior opening 31 through which objects of choice may be placed in the phantom for x-ray adjustment or study. This chamber is sealed against entry of liquid from within the phantom, but if the object to be studied is desired to be in liquid, additional liquid can be placed in the chamber 30. One of the main advantages of this chamber is that an ionization chamber, for example, a pocket dosimeter of the kind commonly worn by x-ray operators to monitor radiation exposure, can be placed in the phantom for diagnostic evaluation of exposure doses reaching the interior tissues of a patient. The particular advantages of using an ionization chamber in the phantom depend to a large degree on the superior simulation of the present phantom to actual human x-ray response characteristics. As mentioned above, the flotation chamber also allows improved x-ray adjustment to locate any specific object in the human body, such as a broken needle.

Other useful objects in the phantom include traditional x-ray machine evaluation and claibration devices such as step wedge type penetrometer 35, wire mesh test pattern 36, and resolution test pattern 37. Stepwedge 35 is used to claibrate the x-ray machine for penetrating power and is well known in the art. Test pattern 36 is used to evaluate radiographic detail or sharpness and also is well known in the art. Resolution test pattern 37 consists of spaced metal bars and has been used in radiography and fluoroscopy to evaluate resolution in the imaging systems. The advantage of locating these devices in the phantom is that their function is evaluated with respect to an environment similar to a human body, leading to optimum machine adjustment for the ultimate goal of taking the best possible x-ray pictures of human patients.

The method of mechanically suspending the various objects in the phantom is a matter of choice, with the preferred method being to attach the objects to a central wall 40 of radiolucent material. The objects may be attached to wall 40 by glue, wire, or screws, or may be embedded in the material of the wall, or may be held in apertures contoured to the shape of the objects.

The liquid scattering medium 14 filling the casing and surrounding x-ray target objects is water-based and contains numerous chemicals. While it has been stated that sea water is the preferred liquid, many substitutes could be used. Pure water could not produce as accurate simulation of human body fluids as sea water, while salt water would be closer in x-ray response characteristics to sea water than is pure water. Human body fluids contain not only salt, but many other elements in small quantities, and the term sea water is intended to include water based compositions of similar composition to natural sea water, whether the composition originates from an ocean or elsewhere, such as being man made.

Radiography detects changes in the atomic number of the target object, and the adjustment of the machine can be difficult when an intended target is in an environment of differing atomic numbers and densities. The similarity between sea water and actual body fluids allows the present invention to simulate the actual scattering effect of body fluid on x-rays. The penetrating power of an x-ray, measured in kilovolts, and the quantity of radiation exposure, measured in milliamperes, can be accurately adjusted for x-ray pictures of the highest quality. The use of the phantom with the described target objects results in the following specific advantages:

1. Allows for evaluation of film qualities for a number of different body densities as compared with a minimal number in conventional phantoms.

2. Shows the effect that a change of kilovolts, milliamperes, or time in seconds have on the film qualities, i.e., density, contrast detail.
3. Show the change in radiation intensity reaching the film when the target-film distance is changed.
4. Allows for showing changes in exposure factors to be made when target-film distance is changed to reduplicate original film qualities.
5. Distortion of the test objects can readily be shown by usual methods used to show this factor.
6. With the optional compartment supplied a change in tissue-thickness can be demonstrated.
7. With the test pattern enclosed detail sharpness changes due to usage of different films, screens, focal spot sizes, motion can be shown.
8. Indicates what modification in KV levels is necessary to show air and fluid levels, as well as polypoids.
9. Establishes techniques which must be used to show variations in the effective atomic number of the test objects enclosed with one exposure.
10. Shows air and fluid levels in the upright or decubitus positions as well as layering of stones in the gallbladder.
11. Illustrates the heel effect as to radiation intensity.
12. Shows change in sharpness of detail due to decreased effective focal spot toward the cathode end of the target.
13. The novel idea of inserting a charged ionization chamber can give readings in exposure doses for different combinations of MA, time in seconds, KV, and distance changes. In addition to the above, the phantom can be used for:
   a. testing radiopacity of newer contrast medias.
   b. comparing screen speed and sharpness of conventional screens against newer marketed ones.
   c. testing speed and contrast of newer films as well as detail sharpness.
   d. calibration of equipment such as imaging systems, setting up proper exposure factors for cine flurography, checking resolution of imaging systems, and setting densities in ionization chambers or photo cells.
   e. checking variations in radiation doses at skin level and at various depths.

These many used and advantages are cited to illustrate the versatile nature of the phantom 10 as an aid to both students of radiography and practicing technicians. While the illustrated embodiment does not physically imitate a human body as do prior phantoms, it is important to note that many critical aspects of x-ray machine adjustment and operation do not require that the target phantom physically resemble a human body, as it is more important that the phantom be versatile in contents and positioning that radiographically simulate human body density. However, the present phantom could be structured to physically resemble a human body or parts thereof if desired.

I claim:

1. An improved x-ray phantom comprising
   (a) a closed casing of radiolucent material,
   (b) a sea water-like liquid filling said casing and serving as an x-ray scattering medium that simulates the x-ray response of human body fluids,
   (c) an x-ray target object mechanically suspended within said casing and liquid for radiographic evaluation.

2. The phantom of claim 1, wherein said sea water-like liquid is sea water.

3. The phantom of claim 1, wherein said target object is a container holding an x-ray contrast media and air, the interface between the air and contrast media allowing the adjustment of x-ray kilovolts to show air and fluid levels within the human body.

4. The phantom of claim 3, wherein the contrast media is barium sulfate.

5. The phantom of claim 3, further comprising polypoid simulations attached to the inner surface of said container.

6. The phantom of claim 1, wherein said target object comprises a container holding x-ray contrast media and gallstone simulations.

7. The phantom of claim 1, wherein said target object comprises a resolution test pattern.

8. The phantom of claim 1, wherein said target object comprises a wire mesh test pattern for evaluating sharpness.

9. The phantom of claim 1, wherein said target object comprises a pentrometer.

10. The phantom of claim 1, further comprising a floatation chamber extending from the surface of said casing into the liquid within the casing and sealed against the fluid within the casing, but having an outer opening for receiving target objects of choice for x-ray.

* * * * *